United States Patent [19]
Panaretto et al.

[11] Patent Number: 4,490,365
[45] Date of Patent: Dec. 25, 1984

[54] DEFLEECING COMPOUNDS

[75] Inventors: Basil A. Panaretto, Cheltenham; Geoffrey P. M. Moore, North Ryde; Duncan M. Robertson, Mosman, all of Australia

[73] Assignee: Commonwealth Scientifique & Industrial Research Organization, Australia

[21] Appl. No.: 553,686

[22] Filed: Nov. 21, 1983

Related U.S. Application Data

[63] Continuation of Ser. No. 287,489, Jul. 7, 1981, abandoned.

[30] Foreign Application Priority Data

Aug. 4, 1980 [AU] Australia .............................. PE4852

[51] Int. Cl.$^3$ .............................................. A61K 37/00
[52] U.S. Cl. ..................................................... 424/177
[58] Field of Search ......................................... 424/177

[56] References Cited

PUBLICATIONS

A. J. Gordon, Aust. J. Of. Exp. Argic. Anim. Husb. 20, 40–49.
J. Biol. Chem. 247, 7609–7611.

Primary Examiner—Delbert R. Phillips
Attorney, Agent, or Firm—Steinberg & Raskin

[57] ABSTRACT

A method of depilating animals, such as sheep, which comprises administering a polypeptide material, which is known as epidermal growth factor or EGF, or analogues thereof to said animals.

6 Claims, 1 Drawing Figure

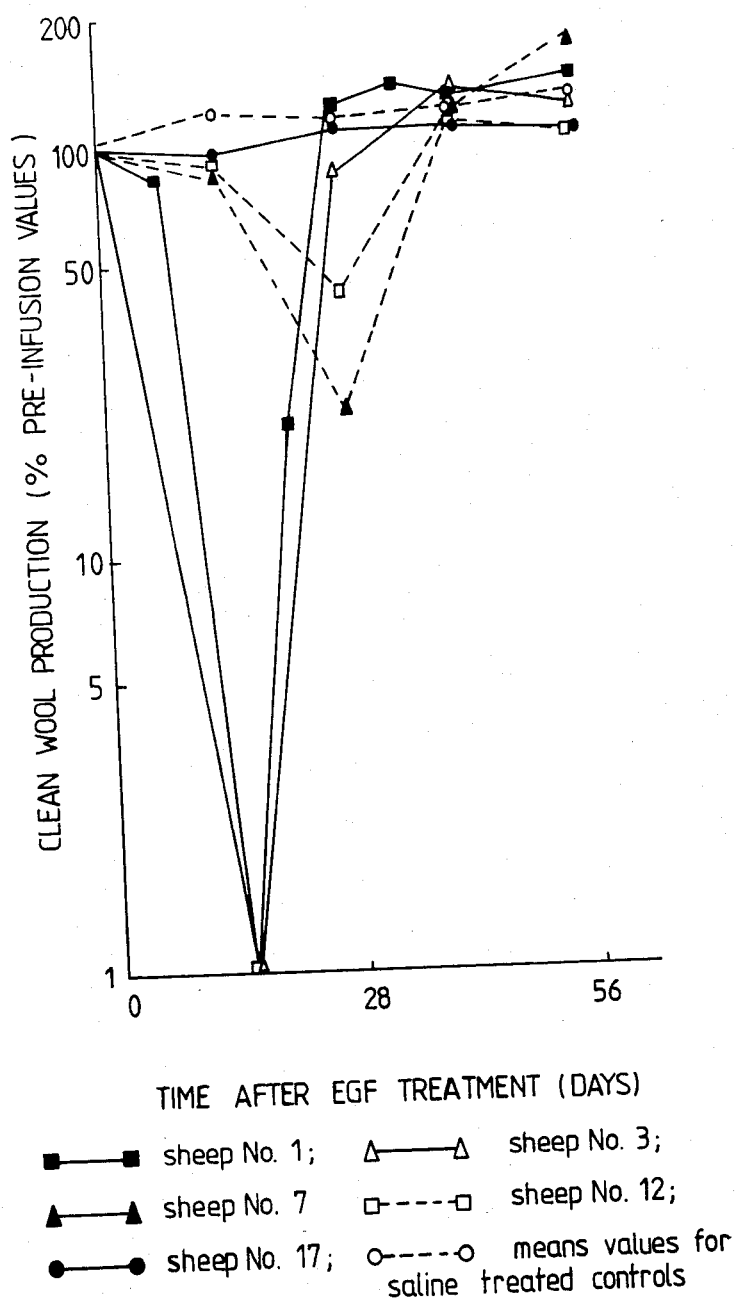
Fig.1 SUBCUTANEOUS INFUSION

DEFLEECING COMPOUNDS

This is a continuation of application Ser. No. 287,489, filed July 7, 1981, now abandoned.

This invention relates to depilating animals by chemical means.

Our Pat. No. 492923 and our co-pending application No. 59755/80 describe the use of compounds, such as mimosine and various phthalimidinopentanes to assist in defleecing sheep. Their effect is to retard wool growth so that, depending on the dose, a zone of weakness is created in the wool fibres or the fleece is cast, both of which conditions can facilitate the mechanical harvesting of wool by unskilled labour. Widescale use of such agents would not, however, be without problems, because the minimum dosage levels for defleecing are very close to the levels at which serious metabolic disturbances can occur.

The present invention is based on the finding that certain substances of animal origin affect wool or hair fibres in a similar way to the aforementioned compounds, but can be administered with safety over a far greater dosage range. Typical of the substances in question is a material isolatable from male mouse salivary glands, which is known as epidermal growth factor or EGF. It has been known for many years that EGF can inhibit body growth rate and hair growth when injected into new born mice, but its ability to control wool growth has not previously been reported.

EGF is a polypeptide of 53 amino acids (EGF 1-53). Although the present invention will be described with particular reference to EGF, what might be termed 'EGF analogues' exhibit similar properties, and may be used instead of EGF as defleecing agents. As well as human EGF, the term 'EGF analogue' as used in this specification embraces the following substances from human, sheep and other species; urogastrone (URO) and fragments thereof, typically URO 1-47, URO 1-52, EGF 1-47, EGF 1-48 and EGF 1-51. Broadly the term includes all synthetic and natural derivatives of the EGF polypeptide family which contain a sequence of amino acids (or amino acid substitutes) effective in regulating hair growth.

Accordingly, in its broadest aspect this invention provides a method for depilating animals which comprises administering to animals EGF or an analogue thereof. In this specification 'depilating' means the removal of wool or hair from animals which are in a metabolic phase wherein wool or hair fibre is being actively produced.

Depilating agents according to this invention may be administered in a variety of ways, but preferably subcutaneously, and dosage regimes may be designed to meet the requirements of specific harvesting means. Although applicable to numerous animal species, such as sheep, goats, and rabbits, the invention will primarily be described with reference to sheep.

One way of defining the extent of wool fibre weakening is by reference to the plucking force (Newtons/ktex, or N/ktex) required to remove the fleece. Methods for making this measurement are described by A. J. Gordon, Aust. J. of Exp. Agric. Anim. Husb. 20, 40–49, and Moore et al, Search. 12, 128–129. We have found that for most harvesting techniques that can be envisaged, if a staple can be removed with a plucking force of between 2–6 N/ktex, then defleecing can be accomplished without causing injury or unacceptable stress to the animal.

Another aspect of this invention is, then, a method of defleecing sheep which comprises administering to sheep EGF or an analogue thereof in an amount sufficient to reduce the mean staple plucking force to at least 6 N/ktex.

Subcutaneous infusion has been found to be a particularly satisfactory means of administering EGF at effective dosage levels. For example in trials reported below, the infusion of EGF at rates as low as 0.16 mg EGF/kg$^{0.75}$(kg$^{0.75}$=metabolic bodyweight) consistently allowed fleece to be easily removed from treated animals. In those experiments administration was via a catheter inserted below the skin. Alternative techniques include, for example, slow release infusion from an implanted capsule or the like, subcutaneous injection or per os.

The invention will now be described in detail by reference to trials in which a number of adult Merino wethers were subjected to various treatments.

PREPARATION OF MATERIALS

EGF was prepared from the submaxillary glands of adult male mice by the method of Savage and Cohen (J. Biol. Chem. 247, 7609–7611).

The derivative EGF 1-45 was prepared by tryptic digestion of the intact peptide as follows: about 25 mg EGF were digested in a small volume of 0.05M phosphate buffer, pH7 with trypsin (50 g, Worthington, TPCK-treated) for 4 hr at 37° C. Subsequently, another 50 g was added and the incubation repeated. The digestate was dialysed overnight at 10° C. in Spectro-Por 6 membrane, and the dialysate freeze dried for storage until required.

ANIMALS

Adult Merino wethers were housed under cover in individual pens or metabolic cages. The animals were offered a maintenance ration of 600 g of a pelleted mixture of 60% lucerne and 40% oats as one meal daily. Drinking water was provided ad lib.

ADMINISTRATION BY SUBSUTANEOUS INFUSION

Wethers were prepared for infusion experiments by the insertion of a polythene catheter below the skin so that the orifice lay near the centre of a 10×10 cm tattooed side on the right midside region of the body. The defleecing agent was dissolved in sterile saline solution and infused using a Harvard pump delivering a volume of 0.030 ml/min. Control animals were infused with saline solution alone. The results are given in detail in Table 1. Broadly, however, it was observed that the infusion of amounts greater than about 0.25 mg EGF/kg$^{0.75}$ resulted in the casing of the whole fleece within about 7 days. With infusions less than 0.25 mg EGF/kg$^{0.75}$ the fleeces were retained but staples could easily be removed by hand.

The amounts of wool harvested from the tattooed area of some animals are shown in Table 1. At dose levels such as 0.74 and 1.86 mg EGF/kg$^{0.75}$ wool production declined to near zero 2 weeks after the start of infusion. Recovery to preinfusion growth levels was observed 2 weeks later. At lower dose levels wool growth inhibition was noticeably less, the maximum recorded effect being about 80% inhibition of wool growth. This occurred about 4 weeks after infusion, but normal wool growth was attained about 2 weeks later.

Infusions of the related peptide EGF 1-45 were found to give closely similar results.

During the course of the above trails blood samples were taken from selected animals at approximately ½ hour intervals after the start of treatment. A correlation between radioimmunoassay determinations of plasma concentrations EGF and forces subsequently required to pluck wool from the skin of the sheep, pointed to the desirability of establishing a plasma concentration EGF of at least about 10 ng/ml for a period of at least about 15 hrs. in order to modify wool growth sufficiently for the fleece to be easily removed by hand.

needed to remove the wool from the animal without causing injury or unacceptable stress to the animal EGF which contains a sequence of amino acids which is effective in regulating hair growth or an analogue of EGF which contains such sequence.

2. A method according to claim 1 wherein said amount is sufficient to reduce the plucking force to a maximum of 6 N/KTex.

3. A method according to claim 1 wherein said amount is sufficient to establish a plasma concentration of said EGF or said analogue thereof of at least about 10 ng/ml for at least about 15 hours.

4. A method according to claim 1 wherein said amount is at least 0.25 mg/kg$^{0.75}$.

TABLE 1

| | SUBCUTANEOUS INFUSION OF EGF, EGF 1-4S OR SALINE | | | | | | |
|---|---|---|---|---|---|---|---|
| Sheep No. | Treatment | Body-weight (kg) | EGF Dose Total | mg/kg$^{0.75}$ | Period of Infusion (hr) | Plucking Force (N/ktex) day 1 | day 9 | Result |
| 1 | EGF | 36.3 | 27.5 | 1.86 | 66 | 12.2 | 0.1 | Fleece cast |
| 2 | Saline | 37.0 | — | — | 66 | 10.4 | 9.0 | No effect |
| 3 | EGF | 41.0 | 11.7 | 0.74 | 28 | 8.9 | 0 | Fleece cast |
| 4 | EGF | — | 11.7 | — | 28 | 3.4 | 0.3(day 7) | Fleece cast |
| 5 | EGF | — | 10.0 | — | 28 | 4.1 | 0.2(day 7) | Fleece cast |
| 6 | Saline | 41.0 | — | — | 28 | 14.3 | — | No effect |
| 7 | EGF | 49.0 | 5.8 | 0.32 | 28 | 7.5 | 0.4 | Fleece cast |
| 8 | EGF | 47.6 | 4.7 | 0.26 | 28 | 21.3 | 2.1 | Fleece cast |
| 9 | EGF | 47.4 | 4.7 | 0.26 | 28 | 12.5 | 1.4 | Fleece cast |
| 10 | EGF | 42.0 | 4.7 | 0.28 | 26.5 | 7.6 | 0.1 | Fleece cast |
| 11 | Saline | 48.0 | — | — | 28 | 6.0 | 7.5 | No effect |
| 12 | EGF | 45.4 | 2.9 | 0.17 | 28 | 6.6 | 0.6 | Weakened fibre |
| 13 | EGF | 30.6 | 2.4 | 0.19 | 25 | 11.3 | 2.1 | Weakened fibre |
| 14 | EGF | 29.4 | 2.0 | 0.16 | 26.5 | 9.3 | 1.5 | Weakened fibre |
| 15 | Saline | 40.1 | — | — | 28 | 3.1 | 5.8 | No effect |
| 16 | EGF | — | 1.0 | — | 28 | 5.5 | 3.6 | Weakened fibre |
| 17 | EGF | 40.8 | 1.0 | 0.06 | 28 | 10.6 | 8.7 | No effect |
| 18 | Saline | 38.6 | — | — | 28 | 8.5 | 6.6 | No effect |
| 19 | EGF | 31.8 | 5.0 | 0.37 | 7 | 7.0 | 0.4 | Fleece cast |
| 20 | EGF | 41.0 | 5.0 | 0.31 | 7 | 17.9 | 1.0 | Fleece cast |
| 21 | EGF | 41.9 | 5.0 | 0.30 | 7 | 11.4 | 0.8 | Fleece cast |
| 22 | EGF | 45.0 | 5.0 | 0.29 | 7 | 9.0 | 1.0 | Fleece cast |
| 23 | EGF | 50.6 | 5.0 | 0.26 | 7 | 12.7 | 2.8 | Fleece cast |
| 24 | EGF | 28.6 | 2.4 | 0.20 | 48 | 14.8 | 3.2 | Weakened fibre |
| 25 | EGF | 28.4 | 2.4 | 0.19 | 48 | 11.7 | 2.4 | Weakened fibre |
| 26 | EGF 1-45 | 42.0 | 4.9 | 0.30 | 26.5 | 5.6 | 0.3 | Fleece cast |
| 27 | EGF 1-45 | — | 1.0 | — | 28 | 4.1 | 3.1 | Weakened fibre |

What we claim is:

1. In a method of depilating a wool bearing animal, the step of reducing the force holding the wool to the animal which comprises administering to such animal in an amount sufficient to reduce the plucking force 5. A method according to claim 1 wherein the administration is subcutaneous.

6. A method according to claim 1 wherein the animal is a sheep.

* * * * *